(12) United States Patent
Wang et al.

(10) Patent No.: US 8,197,831 B2
(45) Date of Patent: *Jun. 12, 2012

(54) STABLE S-(+)-ABSCISIC ACID LIQUID AND SOLUBLE GRANULE FORMULATIONS

(75) Inventors: Yueh Wang, Arlington Heights, IL (US); Prem Warrior, Green Oaks, IL (US); Ahsan Lone, Bartlet, IL (US); John Lopez, Gurnee, IL (US); Bruce Baldi, Libertyville, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 1105 days.

This patent is subject to a terminal disclaimer.

(21) Appl. No.: 12/011,825

(22) Filed: Jan. 30, 2008

(65) Prior Publication Data

US 2008/0254988 A1    Oct. 16, 2008

Related U.S. Application Data

(60) Provisional application No. 60/898,535, filed on Jan. 31, 2007.

(51) Int. Cl.
  *A61K 8/02*    (2006.01)
(52) U.S. Cl. ...................................................... 424/401
(58) Field of Classification Search .................. None
  See application file for complete search history.

(56) References Cited

U.S. PATENT DOCUMENTS

| | | | |
|---|---|---|---|
| 4,209,530 A | 6/1980 | Visscher | |
| 4,434,180 A | 2/1984 | Visscher | |
| 5,583,089 A * | 12/1996 | Winston | 504/101 |
| 6,004,905 A | 12/1999 | Abrams et al. | |
| 6,984,609 B2 * | 1/2006 | Devisetty et al. | 504/116.1 |
| 2002/0114821 A1 | 8/2002 | Lescota et al. | |

FOREIGN PATENT DOCUMENTS

JP    7 165702    6/1995

OTHER PUBLICATIONS

Kim et al., Tetrahedron Lett 38: 1797-1800 (1997).*
Mauseth, "Botany an introduction to plant biology", 1991 Philadelphia Saundera pp. 348-415.
Raven et al., Biology of plants fifth edition, 1992 New York Worth. pp. 545-572.
Milborrow, "The chemistry and physiology of abscisic acid", Am. Rev. Plant Physiol. 1974, 25 pp. 259-307.
Zeevart et al., "Metabolism and physiology of abscsic acid", 1988 Ann. Rev. Plant Physiol. Plant Mol. Biol. 39, pp. 439-473.
Finkelstein et al., "Abscisic Acid Biosynthesis and Response", 2002 The Arabidopsis Book, American Society of Plant Biologists, pp. 1-52.
Mauk et al., "Physiological effects of temperature and growth regulators on foliar chlorophyll, soluble protein, and cold hardiness in citrus", Plant Growth Regulation. 1987, vol. 5, pp. 141-154.
Ruger et al., "Abilities of some antioxidants to stabilize soybean oil in industrial use conditions", JAOCS, 2002, vol. 79, pp. 733-736.
EP Search Report issued Sep. 26, 2011.
Hellman et al., "Exogenously applied abscisic acid did not consistently delay budburst of deacclimating grapevines", Journal of the American Pomological Society, vol. 60, No. 4, 2006, pp. 178-186, XP007919406.
Brabham et al., " Cis-trans photoisomerization of abscisic acid", Photochemistry and Photobiology, vol. 34, No. 1, Jul. 1, 1981, pp. 33-37, XP55006798.
Lindoo et al., "Effects of ultraviolet-B radiation stress on the abscisic acid status of rumex patientia leaves", Physiol. Plant, vol. 45, 1979, pp. 67-72, XP007919410.

* cited by examiner

*Primary Examiner* — Johann Richter
*Assistant Examiner* — Thor Nielsen
(74) *Attorney, Agent, or Firm* — Wood, Phillips, Katz, Clark & Mortimer

(57) ABSTRACT

The present invention generally relates to stable S-(+)-abscisic acid liquid and soluble granule formulations and methods of making and using such formulations.

4 Claims, No Drawings

STABLE S-(+)-ABSCISIC ACID LIQUID AND SOLUBLE GRANULE FORMULATIONS

FIELD OF THE INVENTION

The present invention generally relates to stable S-(+)-abscisic acid liquid and soluble granule formulations and methods of making and using such formulations.

BACKGROUND OF THE INVENTION

Abscisic acid is a naturally occurring plant hormone which acts primarily to inhibit growth, maintain dormancy of buds, promote fruit maturation or coloration, activate the pathogen resistance response defense, induce senescence in already-damaged cells and their proximate neighbors, and help the plant tolerate stressful conditions. See Arteca, R. (1996), *Plant Growth Substances: Principles and Applications*. New York: Chapman & Hall; Mauseth, J. D. (1991), *Botany: An Introduction to Plant Biology*. Philadelphia: Saunders. pp. 348-415; Raven, P. H., Evert, R. F., and Eichhorn, S. E. (1992), *Biology of Plants*. New York: Worth. pp. 545-572.

Abscisic acid owes its name to the belief that this plant growth regulator causes the abscission of leaves from deciduous trees in the fall. Absicin II and dormin are names previously used for this plant hormone. The chemistry and physiology of abscisic acid and its analogs is described by Milborrow, Ann. Rev. Plant Physiol. 1974, 25, 259-307.

The naturally occurring form of abscisic acid is S-(+)-abscisic acid. It has been reported that R-(−)-abscisic acid also has some biological activities. See, Zeevart J. A. D. and Creelman, R. A. (1988) *Metabolism and Physiology of Abscisic Acid*, Annu. Rev. Plant Physiol. Plant Mol. Biol. 39, 439-473. The side chain of naturally occurring abscisic acid is by definition 2-cis, -4-trans.

Abscisic acid was first defined in the early 1960s as a growth inhibitor accumulating in abscissing cotton fruit and leaves of sycamore trees photoperiodically induced to become dormant. See, Finkelstein R R, Rock C D (2002), *Abscisic Acid Biosynthesis and Response*, The Arabidopsis Book Vol. 45, No. 1 pp. 1-48. Since then, abscisic acid has been shown to regulate many aspects of plant growth and development, including embryo maturation, seed dormancy, germination, cell division and elongation. Although abscisic acid has historically been thought of as a growth inhibitor, young tissues have high abscisic acid levels, and abscisic acid-deficient mutant plants are severely stunted because their ability to reduce transpiration and establish turgor is impaired. Exogenous abscisic acid treatment of mutants restores normal cell expansion and growth.

Abscisic acid is thought to initiate its effects on cells through binding to receptor proteins, although their identities and locations are still largely unknown. Activation of the putative receptor(s) causes a chain of events that results in rapid changes in ion channels and slower changes in the pattern of gene transcription. While many individual components of this chain of events have been identified, a complete picture has not yet been obtained.

Commercial formulations comprising abscisic acid are used in the agricultural industry for various purposes, such as to increase crop yield, to advance fruit maturity and color development, to improve stress tolerance, to slow the growth rate, to adjust the flowering phase and for other uses. Abscisic acid has also been reported to possess insect inhibition qualities. See U.S. Pat. Nos. 4,434,180 and 4,209,530 to Visscher. Contents of these patents are herein incorporated by reference. Abscisic acid in a powdered form is currently commercially available from Lomon Biotechnology Company, Ltd., a Chinese company, which markets it as a substance that, among other uses, improves the yield and quality of certain crops.

However, one of the problems associated with industrial use of abscisic acid formulations is relatively poor storage stability of solvent-based abscisic acid liquid formulations, hydroxylation inactivation of 8' and 9' methyl groups in plants (U.S. Pat. No. 6,004,905) and sunlight induced degradation and isomerization of active 2-cis, 4-trans-S-(+) abscisic acid into the inactive 2-trans, 4-trans-S-(+)-abscisic acid isomer. See, Kamuro Y. 1994. Plant and Chemical Regulation 29: 155-165.

On May 30, 2006, the California Department of Pesticide Regulation (DPR) announced an air quality initiative to reduce pesticide-related emissions of volatile organic compounds (VOC). All pesticide formulations sold in California have to meet <30% VOC content as estimated by thermogravimetry analysis (TGA).

U.S. Pat. No. 6,984,609 to Divesetty et al. discloses water soluble granular compositions of at least one plant growth regulator, preferably a gibberellin, a disaccharide and a surfactant.

Therefore, there is an unmet need in the art for stable S-(+)-abscisic acid formulations for commercial applications as well as for the development of low-VOC solid or liquid formulations to meet regulatory requirements.

SUMMARY OF THE INVENTION

The present invention is generally directed to stable S-(+)-abscisic acid (S-ABA) liquid and soluble granule formulations. The stable liquid formulations are generally achieved by adding an effective amount of an antioxidant and an ultraviolet absorber to S-(+)-abscisic acid.

The present invention is also generally directed to stable low VOC S-(+)-abscisic acid (S-ABA) liquid formulations. The low VOC stable liquid formulations are generally achieved by adding an effective amount of an antioxidant, a surfactant, and a wetting agent to S-(+)-abscisic acid in a low VOC solvent system.

In a presently preferred embodiment, the formulation will include an effective amount of an alcohol ethoxylate non-ionic surfactant.

In another presently preferred embodiment, the formulation will include an effective amount of a dioctyl sulfosuccinate anionic surfactant or wetting agent.

In yet another presently preferred embodiment, the formulation will include an effective amount of an alcohol ethoxylate non-ionic surfactant, an effective amount of a propyl gallate antioxidant and a dioctyl sulfosuccinate anionic surfactant or wetting agent.

Presently preferred low VOC solvent systems are based upon high boiling point solvents such as polyethylene glycol of 400 molecular weight. However, these solvent systems can contain other solvents such as lower molecular weight polyethylene glycols or an N,N-dimethyloctanamide/decanamide cosolvent.

The present invention is also directed to liquid compositions for regulating plant growth comprising an effective amount of 2-cis, 4-trans-(S)-abscisic acid and effective amounts of an antioxidant and an ultraviolet absorber.

The present invention is also directed to liquid compositions comprising an effective amount of 2-cis, 4-trans-(S)-abscisic acid in conjunction with an effective amount of a different plant growth regulator and effective amounts of an antioxidant and an ultraviolet absorber. Low VOC solvents such as polyethylene glycol (PEG 300 and 400) can be used in liquid formulations.

In a preferred embodiment, gibberellic acid (GA$_3$), 6-benzyladenine (6-BA) or N-(2-chloro-4-pyridinyl)-N'-phenylurea (CPPU) is the different plant growth regulator.

The present invention is also directed to soluble granule compositions comprising S-ABA, a lactose powder or a sucrose powder, a nonionic surfactant and/or a hydrolyzed starch binder. In a preferred embodiment, the binder is a maltodextrin with about 10% dextrose equivalence (Maltrin M100) and/or a gelled alcohol ethoxylate surfactant (Brij 98).

The present invention is also directed to a process of making soluble 2-cis, 4-trans-(S)-abscisic acid granule compositions by a low-pressure extrusion process.

The disclosed embodiments are simply exemplary embodiments of the inventive concepts disclosed herein and should not be considered as limiting, unless the claims expressly state otherwise.

DETAILED DESCRIPTION OF THE INVENTION

The present invention relates to stable S-(+)-abscisic acid liquid and soluble granule formulations and methods of using these formulations to improve the storage and light stability of 2-cis, 4-trans-(S)-abscisic acid. More specifically, the present invention relates to methods of improving the storage stability and the photochemical stability of 2-cis, 4-trans-(S)-abscisic acid comprising adding an effective amount of at least one antioxidant and an ultraviolet (UV) absorber to the formulation.

Abscisic acid is an optically active 15-C weak acid with 8', 9' and 10' CH$_3$ groups in the ring. The structural formula of abscisic acid is set forth below:

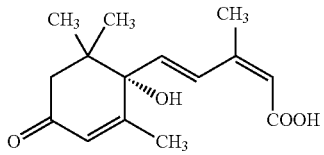

The formulations of the present invention utilize the S-(+) enantiomer rather than a racemic mixture of stereoisomers. Unless expressly stated otherwise, in all instances when the application refers to abscisic acid, it refers to S-(+)-abscisic acid. As used herein, all numerical values relating to amounts, weight percentages and the like, are defined as "about" or "approximately" each particular value plus or minus 10%. For example, the phrase "greater than 0.1%" is to be understood as encompassing values greater than 0.09%. Therefore, amounts within 10% of the claimed values are encompassed by the scope of the claims.

As used in the present invention, the term "antioxidant" means any chemical or biological compound or substance that inhibits oxidation.

As used in the present invention, the term "UV absorber" means any chemical compound or substance that acts to absorb UV light in order to reduce the degradation and the isomerization of 2-cis, 4-trans-(S)-ABA caused by UV radiation.

The phrase "effective amount" of an antioxidant or an ultra violet absorber means a nontoxic but sufficient amount of antioxidant or UV absorber to provide the desired effect. The amount of antioxidant or ultra violet absorber that is "effective" will vary from composition to composition, depending on the particular composition, the particular antioxidant or ultra violet absorber, and the like. Thus, it is not always possible to specify an exact "effective amount." However, an appropriate "effective amount" in any individual case may be determined by one of ordinary skill in the art using routine experimentation. This amount is generally at least 0.1 weight % of the antioxidant and at least 0.1 weight % UV absorber based upon the total weight of the formulation.

Applicants discovered that adding an effective amount of at least one antioxidant can significantly improve storage stability of 2-cis,4-trans-(S)-abscisic acid. Without antioxidants, S-ABA degrades over time; probably, the reason is due to oxidative degradation of the S-ABA molecule which has a highly conjugated structure. Addition of antioxidants likely helps to negate this effect.

In addition, the active 2-cis,4-trans-(S)-abscisic acid tends to izomerize into the inactive 2-trans,4-trans-(S) isomer. Applicants have unexpectedly discovered that addition of an ultra violet absorber greatly slows down the isomerization. The slowdown was demonstrated through High Performance Liquid Chromatography (HPLC) assays.

In one preferred embodiment, the antioxidant is t-butylhydroquinone (TBHQ). In another preferred embodiment, the antioxidant is propyl gallate. In another preferred embodiment, the antioxidant is clove oil. In yet another preferred embodiment, the antioxidant is ethoxyquin.

In one preferred embodiment, the UV absorber is benzophone-3. In another preferred embodiment, the UV absorber is ethylhexyl methoxycinnamate.

A presently preferred composition of the present invention comprises from 1 to 50 weight % S-ABA, from 0.1 to 2.5 weight % antioxidant and from 0.1 to 10 weight % UV absorber. The compositions can also contain from 1 to 20 weight % surfactant and will contain from 40 to 98 weight % solvent. The compositions can then be diluted prior to use as is well known in the art to apply an effective amount of S-ABA to plants being treated as is hereinafter discussed.

Liquid formulations of the present invention can be prepared as either ready-to-use dilutions or dilutable concentrates. According to the present invention, an antioxidant and an ultra violet absorber improve the storage stability and photochemical stability of various dilutions of abscisic acid. The dilutable concentrates can be diluted to a final application concentration or to any intermediate dilution, without risk of precipitation of the active ingredient. The formulations according to the present invention are inexpensive to manufacture, stable under storage and shipping conditions, and are safe to handle and use. A person having ordinary skill in the art would be able to determine how to prepare the dilutions without undue experimentation.

(S)-(+)-abscisic acid has various agricultural applications. For example, formulations of this invention may be used to improve stress tolerance of plants, slow the growth rate, adjust the flowering phase, treat seeds, inhibit the growth of stalk leaf, prevent pre-harvest fruit and flower drop, improve the quality and color of fruits, etc. It is beneficial and highly useful for solutions and granule formulations of abscisic acid to be stable for a long period of time, saving the end user's time and money associated with buying new solutions and/or granule formulations. Possible uses would include, for example, distribution and sale of solutions of compositions comprising (S)-(+)-abscisic acid, an antioxidant, and an UV absorber according to the present invention. The end user could then store the solution for a prolonged period of time as compared with abscisic acid compositions not containing the claimed components. Moreover, because the UV absorber inhibits the formation of the inactive isomer of abscisic acid, the end user would probably be able to use less abscisic acid to achieve his needs since more of the abscisic acid would be in the active form.

In a preferred embodiment, a composition would also include an effective amount of either an alcohol ethoxylate nonionic surfactant and/or dioctyl sulfosuccinate anionic surfactant to solubilize benzophenone or methoxycinnamate and to improve wetting, spray retention and penetration of S-ABA in use dilutions.

In a more preferred embodiment, the surfactants Tomadol® which is a $C_{11}$ alcohol ethoxylate surfactant and is available from Tomah Products Inc. of Milton, Wis., Brij which is a $C_{18}$ alcohol ethoxylate surfactant and is available from Uniqema of Wilimington, Del., and, Monawetg which is a dioctyl-sulfosuccinate anionic surfactant and is available from Uniqema of Wilimington, Del. may be used.

In another aspect, the invention relates to stable S-ABA soluble granule formulations prepared by a low-pressure extrusion process and containing water-soluble lactose or sucrose diluent or filler. The low-pressure extrusion process usually encompasses the dry mixing of dioctyl sulfosuccinate wetting agent with S-ABA and lactose or sucrose powder as well as maltodextrin powder, followed by wetting the resultant blend with a non-ionic surfactant binder solution and mixing the components into a homogenous paste suitable for extrusion. The moist paste can then be extruded into uniform pellets through a perforated screen or other means.

In another aspect, the present invention also relates to liquid compositions comprising an effective amount of 2-cis, 4-trans-(S)-abscisic acid and an effective amount of a different plant growth regulator. The mixtures of S-ABA with other plant growth regulators can improve plant growth, crop yield, stress tolerance, and disease resistance, as well as promote floral bud initiation and flowering.

The following examples are intended to illustrate the present invention and to teach one of ordinary skill in the art how to make and use the invention. They are not intended to limit the invention or its protection in any way.

The following abbreviations are used in the examples:
S-ABA is S-(+)-abscisic acid, a PGR;
6-BA is 6-benzyladenine, a PGR;
CPPU is N-(2-chloro-4-pyridinyl)-N-phenylurea, a PGR;
UV absorber is ultra violet absorber;
TBHQ is tertiary butylhydroquinone, an antioxidant;
Tenox PG is propyl gallate, an antioxidant;
BP-3 is benzophenone-3, a UV absorber;
Escalol® 567 is benzophenone-3, a UV absorber, available from ISP Inc.;
Escalol® 557 is ethylhexyl methoxycinnamate, a UV absorber, available from ISP Inc.;
Tomadol® 1-7 is C11 alcohol ethoxylate, a nonionic surfactant solubilizer, available from Tomah Products, Inc.;
Maltrin® M100 is malodextrin powder of 10% dextrose equivalent available from Grain Processing Corp. of Muscatine, Iowa;
Aerosol® OT-B is 85% sodium dioctyl sulfosuccinate powder;
Monawet® MO84R2W is 84% sodium dioctyl sulfosuccinate anionic wetting agent in propylene glycol solvent;
Brij 97 is oleyl ether polyoxyethylene nonionic surfactant with 10 mole EO;
Brij 98 is oleyl ether polyoxyethylene nonionic surfactant with 20 mole EO;
Tween 20 is sorbitian monolaurate polyoxyethylene nonionic surfactant with 20 moles EO;
PEG 300 or 400 is polyethylene glycol with average 300 or 400 molecular weight;
$GA_3$ tech is a powder of 90% gibberellic acid, a plant growth regulator (PGR);
6-BA tech is a powder of 99% 6-BA, a plant growth regulator (PGR);
CPPU tech is a powder of 98% CPPU, a plant growth regulator (PGR); and
$GA_4A_7$ tech is a powder of 90% $GA_4A_7$, a plant growth regulator (PGR).

EXAMPLE 1

Stability of 1% S-ABA Propylene Glycol Formulations

TABLE 1

| Adjuvant | Form. A | Form. B | Form. C | Form. D | Form. E |
|---|---|---|---|---|---|
| 0.1% antioxidant | No | 0.1% TBHQ | 0.1% PG | 0.1% Ethoxyquin | 0.1% PG |
| 0.2% UV absorber | No | No | No | No | BP-3 |

Five formulations of 1% S-ABA were prepared in propylene glycol solvent as set forth in Table 1 above.

The MT 46 accelerated storage stability test (measurement of degradation of S-ABA at 54° C. after 30 days) was performed on formulations A through C. (Based on CIPAC (collaborative International Pesticides Analytical Concil Limited) handbook F: Physicol-Chemical Methods for Technical and Formulated Pesticides. 1995. A regular storage stability test was performed test (measurement of degradation of S-ABA at 25° C. after 11 months) was performed on formulations A through E. The results are summarized in Table 2 below.

TABLE 2

| Amount of S-ABA as Measured by HPLC Assays (%) | | | | | |
|---|---|---|---|---|---|
| | Form. A | Form. B | Form. C | Form. D | Form. E |
| Initial | 100 | 100 | 100 | 102 | 100 |
| 54° Cel./30 days | 84 | 101 | 98 | N/A | N/A |
| 25° Cel./11 months | | | | | |
| 2-cis, 4-trans | 66 | 103 | 101 | 98 | 100 |
| 2-trans, 4-trans | 1 | 1 | No | 2 | No |

As Table 2 demonstrates, Formulation A, which contained no antioxidant, experienced significant degradation of S-ABA in propylene glycol solvent during storage at 54° C. for 30 days. Without protection, Formulation A lost about 16% after 30 days. In contrast, Formulation B and Formulation C, which contained respectively a TBHQ antioxidant and a PG antioxidant, did not degrade.

Similarly, Formulation A lost another 18% during the regular 25° C. stability test, while the formulations containing antioxidants did not display any loss at the same storage conditions. The results suggest that the storage loss of Formulation A may be due to oxidative degradation of S-ABA molecule that has a highly conjugated structure.

EXAMPLE 2

Photochemical Stability of 1% S-ABA Liquid Formulations

Photochemical stability studies on five 1% S-ABA liquid formulations with and without UV absorber and antioxidant (See Table 3) were conducted in the greenhouse under a 1000 Watt lamp (HI-TEK® Lightning). All formulations were diluted to 50-60 ppm S-ABA with deionized water and were stored in clear glass vials. HPLC assays were performed after 6, 25, and 48 hours exposure times to measure 2-cis,4-trans and 2-trans,4-trans-(S)-ABA concentrations as shown in Table 4.

TABLE 3

Photochemical Stability of 1% S-ABA Liquid Formulations With and Without Antioxidant and UV Absorber

| Ingredients | Form. A | Form. F | Form. G | Form. H | Form. I |
|---|---|---|---|---|---|
| | | | Weight % | | |
| S-ABA (90%) | 1.11 | 1.11 | 1.11 | 1.11 | 1.11 |
| Propylene Glycol | 93.89 | 96.48 | 90.28 | 91.48 | 90.28 |
| Propylene Carbonate | N/A | N/A | 5.0 | 5.0 | 5.0 |
| Tenox PG (99%) | N/A | 0.11 | 0.11 | 0.11 | 0.11 |
| Citric Acid (Anhydrous) | N/A | 0.1 | 0.1 | 0.1 | 0.1 |
| Escalol ® 567 | N/A | 0.2 | 0.4 | N/A | N/A |
| Escalol ® 557 | N/A | N/A | N/A | 0.2 | 0.4 |
| Tomadol ® 1-7 | 5.0 | 2.0 | 3.0 | 2.0 | 3.0 |

TABLE 4

UV Isomerization and Degradation of 1% S-ABA Formulations in Water Dilutions

| Formulation | S-ABA Concentration (ppm) | | | | (Weight %) |
|---|---|---|---|---|---|
| | Initial | 6 hours | 25 hours | 48 hours | |
| Form. A (Control) | | | | | |
| 2-cis, 4-trans | 53.46 | 40.83 | 29.38 | 26.1 | 53.5 |
| 2-trans, 4-trans | 0 | 10.54 | 20.51 | 22.64 | 46.5 |
| % S-ABA loss | 0 | 3.9 | 6.69 | 8.83 | |
| Form. F | | | | | |
| 2-cis, 4-trans | 61.4 | 54.26 | 44 | 36.76 | 63.1 |
| 2-trans, 4-trans | 0 | 6.6 | 16.03 | 21.46 | 36.9 |
| % S-ABA loss | 0 | 0.88 | 2.3 | 5.17 | |
| Form. G | | | | | |
| 2-cis, 4-trans | 61.14 | 56.66 | 47.75 | 40.67 | 69.1 |
| 2-trans, 4-trans | 0 | 4.6 | 12.03 | 18.18 | 30.9 |
| % S-ABA loss | 0 | 0 | 2.23 | 3.75 | |
| Form. H | | | | | |
| 2-cis, 4-trans | 58.77 | 50.28 | 37.74 | 31.03 | 56.2 |
| 2-trans, 4-trans | 0 | 7.96 | 19.08 | 24.22 | 43.8 |
| % S-ABA loss | 0 | 0.9 | 3.31 | 6 | |
| Form. I | | | | | |
| 2-cis, 4-trans | 58.38 | 51.76 | 40.51 | 33.55 | 60.0 |
| 2-trans, 4-trans | 0 | 6.94 | 16.71 | 22.41 | 40.0 |
| % S-ABA loss | 0 | 0 | 2.00 | 4.82 | |

In this Example, glass vials with S-ABA formulations were kept under 1000 Watt greenhouse light at 85° F. temperature. As Table 4 demonstrates, the presence of approximately 10 to 25 ppm of benzophenone-3 or ethylhexyl methoxycinnamate UV absorber and 5-6 ppm of propyl gallate antioxidant in 50-60 ppm 2-cis, 4-trans-S-ABA solutions, resulted in a reduction of the isomerization to the 2-trans, 4-trans-S-ABA and a reduction of the total S-ABA degradation. Formulation A reached 53.5%: 46.5% 2-cis/2-trans mixture after 48 hours exposure and showed 8.83% S-ABA loss. In comparison, Formulation G with estimated 25 ppm of benzophenone-3 UV absorber and 6 ppm propyl gallate antioxidant exhibited 69.1%:30.9% 2-cis/2-trans mixture and 3.75% degradation after 48 hours of light exposure. Moreover, the increase of benzophenone-3 concentration from 0.2% in Formulation F to 0.4% in Formulation G reduced the isomerization rate and S-ABA degradation.

Propylene carbonate solvent and Tomadol® non-ionic surfactant were included in liquid formulations to improve the solubility of water-insoluble benzophenone-3 or ethylhexyl methoxycinnamate UV absorber in liquid formulations or in use dilutions for S-ABA light protection. These antioxidant and UV absorber studies demonstrate that a stable and active S-ABA liquid product can be obtained by adding sufficient antioxidant and UV absorber in the formulation.

EXAMPLE 3

Development of Stable S-ABA Liquid Formulations

TABLE 5

| Ingredients, weight % | Form. K | Form. L | Form. M | Form. N | Form. O | Form. P | Form. Q |
|---|---|---|---|---|---|---|---|
| S-ABA Tech (90%) | 1.12 | 1.12 | 1.12 | 2.22 | N/A | N/A | N/A |
| S-ABA Tech (96.2%) | N/A | N/A | N/A | N/A | 5.28 | 5.28 | 2.6 |
| Propylene Glycol | 98.88 | 96.86 | 71.65 | 93.75 | 83.09 | 83.09 | 47.15 |
| Ethyl lactate | N/A | N/A | 21.7 | N/A | N/A | N/A | N/A |
| Glycerine | N/A | N/A | N/A | N/A | N/A | N/A | 50.0 |
| Tenox PG | N/A | 0.13 | 0.13 | 0.25 | 0.25 | N/A | .25 |
| Clove Oil | N/A | N/A | N/A | N/A | N/A | 0.25 | N/A |
| Citric Acid, Anhydrous | N/A | 0.1 | 0.1 | 0.2 | 0.25 | 0.25 | N/A |
| Escalol ® 557 | N/A | N/A | 0.15 | N/A | N/A | N/A | N/A |
| Escalol ® 567 | N/A | N/A | 0.15 | N/A | N/A | N/A | N/A |
| Monawet MO84R2W | N/A | 1.79 | 2.50 | 3.58 | 6.05 | 6.05 | N/A |
| Brij 97 | N/A | N/A | N/A | N/A | 5.08 | 5.08 | N/A |
| Brij 98 | N/A | N/A | 1.5 | N/A | N/A | N/A | N/A |
| Tween 20 | N/A | N/A | 1.0 | N/A | N/A | N/A | N/A |

TABLE 6

Storage Stability in Brown PE Bottles (S-ABA concentration, weight units)

| Time | Form. K | Form. L | Form. M | Form. N | Form. O | Form. P | Form. Q |
|---|---|---|---|---|---|---|---|
| Initial | 0.99 | 1.01 | 0.99 | 2.05 | 5.11 | 5.12 | 2.51 |
| 2 weeks/54° C. | N/A | N/A | N/A | N/A | 5.14 | 5.08 | 2.60 |
| 33 days/54° C. | 0.92 | 1.04 | 1.04 | N/A | N/A | N/A | N/A |
| Ambient/21 months | 0.25 (75% loss) | 1.09 | 1.09 | 2.13 | N/A | N/A | N/A |

As Table 6 demonstrates, Formulation K without antioxidant protection (control) showed 8% loss at accelerated conditions in a glass vial and 75% loss in ambient storage in brown PE bottles after 21 months. The CIPAC 54° and two or four weeks storage tests may not be able to measure the long term shelf life for S-ABA liquid formulations due to oxidative degradation over time. However, they can predict the stability of a formulation as shown in Formulations L and M if there is no degradation at 54° C. after 2 or 4 weeks storage.

All Tenox PG formulations demonstrated good storage stability with no S-ABA degradation or 2-cis, 4-trans to 2-trans, 4-trans S-ABA isomerization. The Clove oil containing 85% Eugenol antioxidant also demonstrated good protection abilities in stabilizing S-ABA in Formulation P.

Formulation O containing Monawet® wetting agent and Brij® gel surfactant has shown good wetting and spray retention in grape field trials. The surface tensions in 100, 200, and 400 ppm S-ABA use dilutions are respectively, 33.0, 31.2, and 31.0 dynes/cm. No tank-mixing adjuvant is required for Formulation O. There may be some solvent loss in PE bottle storage of Formulations L, M, or N after 21 months. These formulations demonstrated higher assay values after storage than values in the initial assays.

EXAMPLE 4

Representative Low VOC S-ABA Liquid Formulations

| | 5% S-ABA Liquids | | |
|---|---|---|---|
| Ingredients, wt % | Form 1 | Form 2 | Function |
| S-ABA Tech (96.2%) | 5.2 | 5.2 | Active |
| PEG 400 | 79.11 | 84.11 | Solvent |
| PEG 300 | 10.0 | | Cosolvent |
| N,N-dimethyloctanamide/decanamide | | 5.0 | Cosolvent |
| Tenox PG | .25 | .25 | Antioxidant |
| Citric Acid | .25 | .25 | PH control |
| Brij 97 | 4.0 | 4.0 | Surfactant |
| MonawetMO84R2W | 1.19 | 1.19 | Wetting agent |
| TGA | 2.91% | 7.24% | |

A below 30% volatile organic compounds in pesticide formulations standard has been proposed by the California Department of Pesticide Regulation to reduce pesticide-related emission (Air Quality Initiative). An estimate of volatile emission potential of pesticide can be measured by Thermogravimetry Analysis (TGA). TGA: Pesticide samples are heated at 115° C. in an environmentally controlled chamber and then held isothermally until the rate of sample mass loss drops below a defined threshold.

Both Form 1 and Form 2 passed the <30% VOC requirement.

EXAMPLE 5

The Combination of S-ABA with Other Plant Growth Regulators (PGRs)

The pre-mixed liquid formulations of S-ABA in combination with other plant growth regulators (PGRs), such as GA3, 6-BA, CPPU, and $GA_4A_7$ have been developed for new uses as shown in Table 7. The joint action of two PGRs can improve and expand the biological effectiveness and performance of S-ABA.

TABLE 7

The Combination of S-ABA with Other PGRs

| Ingredients, weight % | Form. S | Form. T | Form. U | Form. V | Form. W |
|---|---|---|---|---|---|
| S-ABA tech (90%) | 1.12 | N/A | N/A | N/A | N/A |
| S-ABA tech (96.2%) | N/A | 2.64 | 4.16 | 4.68 | 2.64 |
| GA3 tech (90%) | 1.10 | 2.77 | N/A | N/A | N/A |
| 6-BA tech (99%) | N/A | N/A | 1.01 | N/A | N/A |
| CPPU tech (98%) | N/A | N/A | N/A | 0.51 | N/A |
| GA4A7 tech (90%) | N/A | N/A | N/A | N/A | 2.77 |
| Propylene Glycol | 87.07 | 83.39 | 83.43 | 83.41 | 83.39 |
| Propylene Carbonate | 5.0 | N/A | N/A | N/A | N/A |
| Tenox PG | 0.11 | 0.2 | 0.2 | 0.2 | 0.2 |
| Citric Acid, Anhydrous | 0.1 | 0.2 | 0.2 | 0.2 | 0.2 |
| Escalol ® 567 | 0.5 | N/A | N/A | N/A | N/A |
| Tomadol ® 1-7 | 5.0 | N/A | N/A | N/A | N/A |
| Monawet MO84R2W | N/A | 6.0 | 6.0 | 6.0 | 6.0 |
| Brij 97 | N/A | 5.0 | 5.0 | 5.0 | 5.0 |

Storage Stability

TABLE 8

S-ABA/GA3 Assays

| Time | Form. S | Form. T | Form. U | Form. V | Form. W |
|---|---|---|---|---|---|
| initial | 0.99/1.05 | 2.66/2.80 | 4.10/NA | 4.64/NA | N/A |
| 54° C./2 weeks | N/A | 2.58/2.41 | 4.10 | 4.59 | N/A |
| Ambient temp./27 months | 1.02/1.03 | N/A | N/A | N/A | N/A |

Formulation S containing 1% S-ABA and 1% $GA_3$ plus an antioxidant and a UV absorber demonstrated excellent chemical stability for both PGRs after 27 months of storage at ambient temperature. In an accelerated test, there was about 14% loss of $GA_3$ in Formulation T at 54° C. storage. High storage temperature may not be a good condition to predict $GA_3$ shelf stability of lactone structure (due to acid hydrolysis at elevated temperature). The presence of $GA_3$, 6-BA or CPPU has not shown adverse effect on S-ABA stability.

EXAMPLE 6

Soluble Granule Formulations

10% and 20% S-ABA soluble granule formulations have been developed with water-soluble sucrose or lactose diluent or filler by low-pressure extrusion process as shown in Table 9. The low-pressure extrusion process was conducted as follows.

Fine S-ABA 90% or 95% technical powder was blended with lactose or sucrose powder as well as Maltrin powder in the presence of 1% Aerosol OT-B wetting agent. The dry blend was easily wetted with Brij non-ionic surfactant binder solution, and then was mixed into a homogenous paste suitable for extrusion. The moist paste was extruded into fine and cylindrical pellets of uniform size through a perforated screen of 1 mm diameter. The small pellets were pan- or fluid-bed dried to less than 1% moisture and were screened through −12/+50 mesh to obtain final soluble granule products.

TABLE 9

10% and 20% S-ABA Soluble Granule Formulations

| Ingredients, weight % | 20% SG Form. X | 10% SG Form. Y | Function |
|---|---|---|---|
| S-ABA tech (96.2%) | 21.05 | N/A | PGR |
| S-ABA tech (90%) | N/A | 11.11 | PGR |
| Lactose Powder | 70.95 | N/A | Diluent |
| Sucrose Powder | N/A | 84.39 | Diluent |
| Citric Acid | 2.0 | 2.5 | pH Control |
| Aerosol OT-B | 1.0 | 1.0 | Wetting agent |
| Water | (10.0) | (9.0) | |
| Maltrin ® M100 | 4.0 | N/A | binder |
| Brij 98 | 1.0 | 1.0 | binder |

TABLE 10

Attrition Resistance and Accelerated Storage Stability

| Attrition Resistance | Form. X | Form. Y |
|---|---|---|
| −80 mesh | 0.14% | 0.2% |
| Accelerated Storage Stability | S-ABA assay (weight %) | |
| Initial | 21.2 | 10.49 |
| 54° C./2 weeks | 21.2 | N/A |

Granular Formulations X and Y were prepared with an LCI Benchtop or Dome Extruder. Only 8-10% of water in conjunction with Brij and binder was required to wet powder mixtures for extrusion. Aerosol® OT-B improved powder wetting to make paste material. Maltrin® and Brij® were found to be strong binders for granulation. The binding systems are different from Valent's 40% ProGibb® Soluble Granules with PVP binder and from emamectin benzoate soluble granules formulations with anionic sodium alkyl naphtalene sulfonate and/or N-methyl N-oleyl taurate surfactant binders (U.S. Pat. App. No. 2002/0114821 A1). Formulations X and Y have shown good attrition resistance (less than 1%-80 mesh dust) in a 2 minute RoTap® shaker test with 15 stainless steel balls.

Formulation X has shown good stability in the accelerated test. The soluble granule formulation of low phytotoxicity is ideal for sensitive young or ornamental plant treatments. All EPA List 4 inerts may be used for S-ABA Soluble Granule formulations and they are all qualified as organic pesticides.

EXAMPLE 7

ABA formulation performance was evaluated in the field using table grape coloration to assess efficacy. Treatments consisted of untreated control, ethephon control (industry standard ethylene-releasing agent), ABA technical (95% ABA solubilized in ethanol), ABA liquid formulation, and ABA water-soluble granule formulation. All treatments had 0.05% v/v Latron B-1956 surfactant included. The three ABA treatments (200 ppm ABA; 200 gallons/acre) and the ethephon control (250 ppm at 200 gallons/acre) were foliar applied with a backpack sprayer at 10 to 20% color development (June 27) on Flame Seedless grapes commercially grown in Arvin, Calif. The numbers of color clusters per 4 vines were assessed at 8 and 11 days after treatment.

Application of ABA technical increased the number of colored clusters more than the ethephon control. More importantly, ABA liquid formulation and ABA water-soluble granule formulation increased the number of colored clusters more than ABA technical. Thus, both formulations were more effective than ABA technical.

TABLE 11

Comparison of ABA Formulations with ABA Technical for Improved Grape Color of Flame Seedless Grapes

| | Number of colored clusters per 4 vines | |
|---|---|---|
| Treatment | 8 days after treatment | 11 days after treatment |
| Untreated control | 0.8 | 1.3 |
| Ethephon control (250 ppm) | 6.0 | 6.7 |
| Technical (200 ppm ABA) | 9.0 | 11.2 |
| Liquid formulation (200 ABA ppm) | 9.8 | 14.7 |
| Water-soluble granule formulation (200 ppm ABA) | 13.8 | 28.5 |

EXAMPLE 8

ABA formulation performance was evaluated in the greenhouse using Coleus wilting to assess efficacy. Treatments consisted of control, ABA technical (95% ABA solubilized in ethanol), ABA liquid formulation, and ABA water-soluble granule formulation. Coleus plants were grown in four-inch diameter pots to the 6 to 8 leaf stage (n=4 plants/treatment). Water (15 mL/plant) was drench-applied to the control plants, and ABA (15 mL/plant; 250 ppm ABA) was drench applied to ABA treated plants. The plants were held in a greenhouse without irrigation until all plants wilted to a point when they were determined to be unmarketable. The plants were rated daily for the extent of wilting on a scale from 1 (no wilting) to 4 (complete wilting). A rating of 2.5 was the point at which a plant was determined to be unmarketable and the previous day was recorded as the marketable life of that plant in days.

Application of ABA technical delayed wilting and increased shelf life of Coleus plants (Table 12). More importantly, ABA liquid formulation and ABA water-soluble granule formulation increased Coleus plant shelf life more than ABA technical. Thus, both formulations were more effective than ABA technical.

TABLE 12

Comparison of ABA Formulations with ABA Technical for Improved Drought Tolerance of *Coleus* Plant

| Treatment | Days of shelf life after treatment |
|---|---|
| Control | 10 |
| Technical (250 ppm ABA) | 12 |
| Liquid formulation (250 ABA ppm) | 13 |
| Water-soluble granule formulation (250 ppm ABA) | 13 |

The invention claimed is:

1. A soluble 2-cis, 4-trans-(S)-abscisic acid granule formulation consisting of:
   a) 2-cis, 4-trans-(S)-abscisic acid powder;
   b) a lactose powder or a sucrose powder;
   c) a sodium dioctyl sulfosuccinate wetting agent;
   d) maltodextrin powder of about 10% dextrose equivalence;
   e) Brij 98;
   f) optionally citric acid;
   g) and optionally water.

2. A soluble 2-cis, 4-trans-(S)-abscisic acid granule formulation consisting of:
   a) about 21.1% by weight of 2-cis, 4-trans-(S)-abscisic acid powder;
   b) about 71.0% by weight of lactose powder;
   c) about 1.0% by weight of a sodium dioctyl sulfosuccinate wetting agent;
   d) about 4.0% by weight of maltodextrin powder of about 10% dextrose equivalence;
   e) about 1.0% by weight of Brij 98;
   f) about 2.0% by weight of citric acid;
   g) and optionally water.

3. A soluble 2-cis, 4-trans-(S)-abscisic acid granule formulation consisting of:
   a) about 21.1% by weight of 2-cis, 4-trans-(S)-abscisic acid powder;
   b) about 71.0% by weight of lactose powder;
   c) about 1.0% by weight of a sodium dioctyl sulfosuccinate wetting agent;
   d) about 4.0% by weight of maltodextrin powder of about 10% dextrose equivalence;
   e) about 1.0% by weight of Brij 98;
   f) and optionally water.

4. A process of making the soluble 2-cis, 4-trans-(S)-abscisic acid granule formulation of claim 1 comprising the steps of
   a) blending the 2-cis, 4-trans-(S)-abscisic acid powder with the lactose or sucrose and the maltodextrin powder in the presence of the sodium dioctyl sulfosuccinate resulting in a formation of a dry blend;
   b) wetting the blend with Brij 98;
   c) mixing the blend of step (b) into a homogenous paste suitable for extrusion;
   d) extruding the paste of step (c) into fine pellets of approximately uniform size; and
   e) drying the pellets of step (d) to less than about 1% moisture.

* * * * *